United States Patent [19]

Castanet et al.

[11] Patent Number: 5,214,205
[45] Date of Patent: May 25, 1993

[54] PROCESS FOR THE PREPARATION OF ACETIC ANHYDRIDE FROM METHYL FORMATE

[75] Inventors: Yves Castanet, Hem; Bruno Seuillet, Compiegne; André Mortreux, Hem; Francis Petit, Villeneuve d'Asq, all of France

[73] Assignee: Sollac, A French Body Corporate, Puteaux, France

[21] Appl. No.: 868,186

[22] Filed: Apr. 14, 1992

[30] Foreign Application Priority Data

Apr. 25, 1991 [FR] France .................. 91 05145

[51] Int. Cl.$^5$ ............. C07C 51/12; C07C 51/10
[52] U.S. Cl. .................. 562/891; 562/890; 562/889; 562/519; 562/517
[58] Field of Search ........... 562/889, 890, 891, 519, 562/512

[56] References Cited

U.S. PATENT DOCUMENTS

| | | | |
|---|---|---|---|
| 3,829,428 | 10/1974 | Isogai et al. | 260/514 |
| 4,194,056 | 3/1980 | Antoniades | 562/517 |

FOREIGN PATENT DOCUMENTS

| | | | |
|---|---|---|---|
| 0087870 | 9/1983 | European Pat. Off. | 562/891 |
| 0132381 | 1/1985 | European Pat. Off. | 562/890 |
| 0144936 | 6/1985 | European Pat. Off. | 562/519 |
| 0170964 | 2/1986 | European Pat. Off. | 562/891 |
| 0135445 | 6/1987 | Japan | 562/891 |

Primary Examiner—José G. Dees
Assistant Examiner—Keith MacMillan
Attorney, Agent, or Firm—Oblon, Spivak, McClelland, Maier & Neustadt

[57] ABSTRACT

The invention relates to a process for the preparation of acetic anhydride, characterized in that a gas containing essentially CO, at a pressure of at least 1 MPa, is reacted with methyl formate in the presence of
a) a rhodium-based catalyst,
b) two iodine-containing promoters of different kind, successively ionic and covalent, and
c) an N-substituted cyclic amide as solvent.

12 Claims, No Drawings

PROCESS FOR THE PREPARATION OF ACETIC ANHYDRIDE FROM METHYL FORMATE

The present invention relates to a process for the preparation of acetic anhydride from methyl formate, which is a new synthesis.

Acetic anhydride is a very important product of organic chemistry and can be obtained industrially especially by carbonylation of methyl acetate. Many documents list this reaction with different catalyst systems based on rhodium (for example patents FR-2,242,362, FR-2,289,480, FR-2,303,597 and EP-A-8,396), cobalt (European patent EP-A-67,777) or nickel (FR-2,336,367).

Similarly, some documents (such as patents BE-A-819,455, U.S. Pat. No. 4,115,444 and FR-A-2,472,556) extend this reaction to the carbonylation of various esters or even ethers to the corresponding carboxylic acid anhydride.

However, none refers to the esters of formic acid, which would result in formic anhydride, too unstable to be isolated, nor describes the direct synthesis of acetic anhydride from methyl formate, a reaction which formally corresponds to a homologue conversion of the formate into methyl acetate, followed by carbonylation of this latter compound.

Such a process of synthesis of acetic anhydride from the formate would be advantageous insofar as it could lead to acetic anhydride from methanol in only two stages instead of three when this synthesis is performed via methyl acetate according to the known art:

Synthesis of Acetic Anhydride

- via methyl acetate

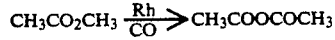

- via methyl formate

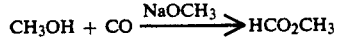

We have now found that this latter reaction can be carried out, with the result that acetic anhydride is accessible from methanol, an inexpensive industrial product.

The present invention thus relates to a process for the preparation of acetic anhydride, characterised in that a gas containing essentially CO, at a pressure of at least 1 MPa, is reacted with methyl formate in the presence of
a) a rhodium-based catalyst,
b) two iodine-containing promoters of different kind, successively ionic and covalent, and
c) an N-substituted cyclic amide as solvent.

The operation is advantageously carried out at a temperature of 100° to 260° C. (temperature above which the stability of the catalyst becomes problematic) and preferably from 150° to 210° C.

A gas containing essentially CO is intended to mean pure CO or a CO-rich gas such as steelworks gas, and this enables this gas to be reclaimed. A steelworks gas has, for example, the following compositions: CO=74.5%, CO$_2$=14.9%, H$_2$=2%, N$_2$=8.3%, O$_2$=0.2%.

The pressure must be at least 1 MPa. This pressure can be kept constant or advantageously increased during the reaction without it being necessary to exceed 15 MPa.

As examples of rhodium-based catalysts, there may be mentioned RhCl$_3$.3H$_2$O, Rh$_2$Cl$_2$(CO)$_4$, RhCOCl(PPh$_3$)$_2$, RhI$_3$, etc, this list not being limiting, since all the Rh salts or complexes tried were found to be active.

As indicated above, the operation is carried out in a particular solvent consisting of an N-substituted cyclic amide. In fact, the nature of the solvent is critical because, without any solvent or in usual solvents other than N-substituted cyclic amides, the selectivity for acetic anhydride is much lower, since acetic acid generally becomes the main product of the reaction via isomerisation of the methyl formate. As an example of N-substituted amide there may be mentioned dimethylimidazole, N-ethylpyrrolidone or, preferably, N-methylpyrrolidone.

The proportion of solvent relative to the starting methyl formate must not be lower than 2 volumes of solvent per 3 volumes of formate, otherwise the production of acetic acid is seen to increase. Above this value the quantity of solvent may be chosen within a wide range, it being nevertheless understood that, at equivalent performance, the tendency will be to employ the smallest possible quantity of solvent so as to limit the reaction volume and to simplify the problems of separation from the solvent of the products formed at the end of the reaction. Proportions of solvent relative to the formate ranging from 1/1 to 3/1 (v/v) will be preferably employed.

The use of iodine-containing promoters is also indispensable. Two types of iodine-containing promoters must essentially be employed in succession in the course of a single reaction.

At the beginning of reaction the mixture must contain an exclusively ionic iodide, it being possible for this ionic iodide to be inorganic, especially an alkali metal one (for example LiI, NaI etc) or an alkaline-earth metal one. This ionic iodine-containing promoter may also be obtained in situ by mixing an organic covalent iodine compound (for example an alkyl iodide) with a phosphine or an amine, resulting in the corresponding quaternary phosphonium or ammonium iodide.

The initial content of ionic iodide must be adjusted as a function of the initial CO pressure; the higher the CO pressure, the higher must be the concentration of ionic iodide; it will be especially in a range extending from 0.1 to 0.5 mol/l.

Furthermore, during the reaction a covalent iodine compound must be added to the reaction mixture. It will be possible for this to be accomplished without it being necessary to stop the reaction, however, for example with the aid of a high-pressure metering pump or by virtue of a ballast system. As an example of covalent iodine compound there may be mentioned organic iodides (alkyl iodide) and preferably CH$_3$I, molecular iodine I$_2$ or hydriodic acid.

The covalent iodide content will be especially from 0.15 to 1 mol/l.

Finally, it is desirable to employ a metal promoter such as Cr(CO)$_6$; although not indispensable for the production of acetic anhydride, this addition results in an increase in activity. This promoter is advantageously employed at a concentration ranging from $5 \times 10^{-1}$ to $3 \times 10^{-2}$ mol/l.

The reaction according to the invention is preferably carried out without any substantial presence of water, because the presence of water has the effect of decreasing the selectivity for acetic anhydride.

The following examples illustrate the process according to the invention.

EXAMPLE 1

The following are introduced into a 100-cm² stainless steel autoclave:
0.03 g ($1 \times 2.10^{-4}$ mol) of $RhCl_3.3H_2O$
1 g ($7 \times 46.10^{-3}$ mol) of LiI
10 ($0.45 \times 10^{-3}$ mol) of $Cr(CO)_6$ 15 g of methyl formate in solution in 15 cm² of N-methylpyrrolidone (NMP).

The autoclave is pressurised to 10 bar (1 MPa) of CO and then heated to 190° C. and stirring is switched on when the temperature has stabilised. After 6 h of reaction, 1.14 g ($8 \times 10^{-3}$ mol) of $CH_3I$ dissolved in 5 cm³ of NMP are injected rapidly into the reaction mixture with a high-pressure metering pump, and the CO pressure is increased by 30 bar (3 MPa), which raises the total pressure on heating to 80 bar (8 MPa). After a further 4 h of reaction, the heating and stirring are switched off and, after cooling, the reaction mixture is analysed by gas phase chromatography.

The results are as follows (expressed in mol % of the various constituents in the mixture):
$HCOOCH_3 = 1.5$
$CH_3COOCH_3 = 14$
$CH_3COOH = 19.5$
$CH_3COOCOCH_3 = 48$

EXAMPLE 2

Example 1 is reproduced, except that the autoclave is initially pressurised to 40 bar (4 MPa) of CO instead of 10 bar, and CO is no longer introduced during the reaction.

The following results are obtained after 10 h of reaction:

$HCOOCH_3 = 3$
$CH_3COOCH_3 = 12$
$CH_3COOH = 35$
$CH_3COOCOCH_3 = 41$

EXAMPLES 3 and 4

Influence of the Quantity of $CH_3I$ Introduced

Example 1 is reproduced, the quantity of $CH_3I$ injected during the reaction being varied.

| Ex. | Quantity of $CH_3I$ (mmol) | % Products | | | |
|---|---|---|---|---|---|
| | | $HCOOCH_3$ | $CH_3COOCH_3$ | $CH_3COOH$ | $CH_3COOCOCH_3$ |
| 1 | 8 | 1.5 | 14 | 29.5 | 48 |
| 3 | 4 | 2 | 47 | 30 | 12 |
| 4 | 16 | 0 | 11.5 | 24 | 54 |

EXAMPLES 5 and 6

Influence of the CO Pressure

Example 1 is reproduced while modifying the quantity of CO introduced so as to obtain the pressure of CO when heated which appears in the following table.

| Ex. | P (CO) (when hot) | % Products | | | |
|---|---|---|---|---|---|
| | | $HCOOCH_3$ | $CH_3COOCH_3$ | $CH_3COOH$ | $CH_3COOCOCH_3$ |
| 1 | 8 MPa | 1.5 | 14 | 29.5 | 48 |
| 5 | 11 MPa | 1 | 11 | 28 | 50 |
| 6 | 5 MPa | 2 | 46 | 30 | 2 |

EXAMPLES 6 and 7

Influence of the Time of Introduction of the Covalent Iodide

| Ex. | Time of introduction of $CH_3I$ | % Products | | | |
|---|---|---|---|---|---|
| | | $HCOOCH_3$ | $CH_3COOCH_3$ | $CH_3COOH$ | $CH_3COOCOCH_3$ |
| 1 | 6 h | 1.5 | 14 | 29.5 | 48 |
| 6 | 3 h | 2.5 | 10 | 83.5 | 4 |
| 7 | 8 h | 1 | 51 | 34 | 14 |

We claim:

1. A process for the preparation of acetic anhydride, wherein a gas containing essentially CO, at a pressure of at least 1 MPa, is reacted with methyl formate in the presence of
   a) a rhodium-based catalyst;
   b) a first iodine-containing promoter of ionic-type, which is present at the beginning of reaction;
   c) a second iodine-containing promoter of covalent-type, which is added during reaction; and
   d) an N-substituted cyclic amide as solvent, wherein the proportion of solvent relative to methyl formate is higher than 2/3 (v/v).

2. The process according to claim 1, wherein the reaction is carried out at temperature of 100° to 260° C.

3. The process according to claim 2, wherein the temperature is from 150° to 210° C.

4. The process according to claim 1 wherein the solvent is N-methylpyrrolidone.

5. The process according to claim 1, wherein the proportion of solvent relative to the formate is from 1/1 to 3/1 (v/v).

6. The process according to claim 1 wherein the first iodine-containing promoter is an alkali metal or alkaline-earth metal iodide.

7. The process according to claim 1 wherein the first iodine-containing promoter is a mixture of an organic covalent iodine compound with a phosphine or an amine.

8. The process according to claim 6 or 7, wherein the iodine-containing promoter is employed at a concentration of 0.1 to 0.5 mol/l.

9. The process according to claim 1, wherein the second iodine-containing promoter is an organic covalent iodine compound.

10. The process according to claim 9, wherein the iodine-containing promoter is employed at a concentration of 0.15 to 1 mol.l.

11. The process according to claim 1, wherein a metal promoter is employed at a concentration of $5 \times 10^{-3}$ to $3 \times 10^{-2}$ mol/l.

12. The process according to claim 11, wherein the metal promoter is $Cr(CO)_6$.